(12) United States Patent
Stridde et al.

(10) Patent No.: US 6,887,830 B2
(45) Date of Patent: May 3, 2005

(54) SURFACTANT ADJUVANTS USEFUL IN HERBICIDE COMPOSITIONS

(75) Inventors: Howard Meyer Stridde, Georgetown, TX (US); Samir S. Ashrawi, Austin, TX (US); David Charles Lewis, Austin, TX (US); Curtis Michael Elsik, Austin, TX (US); Andrew Francis Kirby, Melbourne (AU)

(73) Assignee: Huntsman Petrochemical Corporation, Austin, TX (US)

( * ) Notice: Subject to any disclaimer, the term of this patent is extended or adjusted under 35 U.S.C. 154(b) by 33 days.

(21) Appl. No.: 10/175,535

(22) Filed: Jun. 18, 2002

(65) Prior Publication Data

US 2003/0032558 A1 Feb. 13, 2003

Related U.S. Application Data

(63) Continuation of application No. 09/718,208, filed on Nov. 21, 2000, now abandoned.
(60) Provisional application No. 60/166,933, filed on Nov. 22, 1999.

(51) Int. Cl.⁷ .......................... A01N 25/30; A01N 57/02
(52) U.S. Cl. ........................................ 504/206; 504/358
(58) Field of Search ................................. 504/206, 358, 504/127, 128

(56) References Cited

U.S. PATENT DOCUMENTS

| 5,612,285 A | * | 3/1997 | Arnold ........................ 504/206 |
| 6,117,820 A | * | 9/2000 | Cutler et al. ................ 504/206 |

FOREIGN PATENT DOCUMENTS

| EP | 0 569 264 | * 11/1993 |

* cited by examiner

*Primary Examiner*—S. Mark Clardy
(74) *Attorney, Agent, or Firm*—Gardere Wynne Sewell LLP

(57) ABSTRACT

Surfactant adjuvants that improve the bioefficacy of herbicides by combining known surfactancy, or wetting characteristics, of sulfosuccinate or sulfosuccinamate-based surfactants, with the proven bioefficiacy characteristics of alkoxylated amine-based surfactants. The surfactant adjuvants contain an amine-based surfactant, and a sulfosuccinate or sulfosuccinamate-based surfactant. The surfactant adjuvants are combined with herbicidal active ingredients, and optionally, one or more formulation aids to form herbicide compositions that have a reduced tendency to cause eye and skin irritation and can be used to control unwanted weeds or vegetation.

25 Claims, No Drawings

SURFACTANT ADJUVANTS USEFUL IN HERBICIDE COMPOSITIONS

CROSS REFERENCE TO RELATED APPLICATIONS

This application is a continuation of U.S. Non-Provisional Application No. 09/718,208 filed on Nov. 21, 2000 now abandoned, which claims the benefit of U.S. Provisional Application No. 60/166,933, filed on Nov. 22, 1999.

TECHNICAL FIELD

This invention relates to adjuvants, and, more particularly, to surfactant adjuvants that enhance the bioefficacy of herbicides.

BACKGROUND OF THE INVENTION

Herbicide compositions are often characterized according to the identity of the active ingredient, and by the mode by which the active ingredient causes vegetation necrosis. Regardless of the active ingredient, most herbicides cause vegetation necrosis by interfering with one or more vital biological processes essential to the vegetation's survival. Yet, before the active ingredient of a herbicide can interfere with such biological processes, the active ingredient must somehow be absorbed into the vegetation. Unfortunately, this absorption is often hindered by the chemical nature of the active ingredient.

Accordingly, in addition to active ingredients, most herbicide compositions also include other components, commonly termed adjuvants, that enhance the performance and absorption of the active ingredient. One class of adjuvants that is frequently used is surfactants. Surfactants are useful in herbicide compositions because they tend to both enhance the absorbing properties of the active ingredient, as well as facilitate application of the herbicide.

Several existing patents disclose various classes of amine-based surfactant adjuvants. For example, U.S. Pat. No. 5,683,958 discloses surfactant compositions comprising polyoxyalkylene alkylamines. U.S. Pat. No. 5,798,310 discloses adjuvants comprising alkoxylated quaternary ammonium surfactants. U.S. Pat. No. 5,668,085 discloses glyphosate formulations comprising alkoxylated amine surfactants. And, U.S. Pat. No. 5,118,444 discloses amine-oxide surfactants produced by oxidizing tertiary polyalkoxylated amine surfactants.

Several existing patents also disclose various sulfosuccinate or sulfosuccinamate-based surfactants that are useful in a variety of applications. For example, U.S. Pat. No. 5,762,757 discloses methods of inhibiting the deposition of organic contaminants from pulp in papermaking and pulp systems through the use of a combination of dioctylsulfosuccinate and didecyl sulfosuccinate anionic surfactants. U.S. Pat. No. 5,480,586 discloses a liquid detergent composition comprising a sulfosuccinamate-containing surfactant blend. U.S. Pat. No. 5,236,710 discloses cosmetic compositions containing an emulsifying copolymer and anionic sulfosuccinate. And, U.S. Pat. No. 5,015,414 discloses a low-irritant detergent composition containing an alkyl saccharide and sulfosuccinate surfactants.

However, the literature appears to lack any reference to the combined use of an amine-based surfactant and a sulfosuccinate or sulfosuccinamate-based surfactant as a herbicide adjuvant. It was discovered that the bioefficacy of amine-based surfactant adjuvants may be enhanced with the addition of a sulfosuccinate or sulfosuccinamate-based surfactant. Accordingly, the present invention is directed toward surfactant adjuvants that comprise an amine-based surfactant and a sulfosuccinate or sulfosuccinamate-based surfactant, herbicide compositions comprising such surfactant adjuvants, and a method of controlling unwanted vegetation using such herbicide compositions.

SUMMARY OF THE INVENTION

The present invention provides for surfactant adjuvants that improve the bioefficacy of herbicides. The surfactant adjuvants comprise an amine-based surfactant and a sulfosuccinate or sulfosuccinamate-based surfactant. The sulfosuccinate or sulfosuccinamate-based surfactant may be derived from linear alcohol alkoxylates, branched alcohol alkoxylates, alkylphenol alkoxylates, or hydroxy-bearing hydrophobes. The amine-based surfactant may comprise an alkoxylated amine, and preferably comprises a cocoamine alkoxylate, tallow amine alkoxylate, soya amine alkoxylate, synthetic alkoxylated amine derived from a primary alcohol, alkydiamine alkoxylate, etheramine alkoxylate, alkyletheramine, alkyletheramine alkoxylate, the methyl and ethyl quaternary ammonium salts thereof, and the amine oxides thereof.

The present invention also provides for herbicide compositions that contain a surfactant adjuvant of the present invention. The herbicide compositions comprise a herbicidal active ingredient, a surfactant adjuvant of the present invention, and optionally, one or more formulation aids. The herbicide compositions of the present invention are expected to have a reduced tendency to cause eye and skin irritation.

The present invention additionally provides for a method of controlling unwanted weeds or vegetation using the herbicide compositions of the present invention.

DETAILED DESCRIPTION OF THE INVENTION

The surfactant adjuvants of the present invention enhance the bioefficacy of herbicides because they combine the known surfactancy, or wetting characteristics, of sulfosuccinate or sulfosuccinamate-based surfactants, with the proven bioefficacy characteristics of amine-based surfactant adjuvants, and, in particular, alkoxylated amine-based surfactant adjuvants.

It was discovered that the surfactant adjuvants of the present invention were compatible with high electrolyte solutions, such as those containing glyphosate. This discovery was unexpected because sulfosuccinate and sulfosuccinamate-based surfactants are not typically compatible with high electrolyte solutions.

Accordingly the surfactant adjuvants of the present invention may be used in conjunction with any number of herbicides or mixtures thereof, including, but not limited to, various salts of glyphosate and glufosinate. However, the use of the surfactant adjuvants of the present invention with glyphosate is of particular interest because glyphosate is probably the most widely used herbicide.

Glyphosate, or N-phosphonomethylglycine, is a broad-spectrum herbicide that is useful on essentially all annual and perennial plants, including, grasses, broad-leaved weeds, and woody plants. Glyphosate promotes plant necrosis by inhibiting aromatic amino acid biosynthesis. By inhibiting aromatic amino acid synthesis, and thereby protein synthesis, glyphosate initially suppresses plant growth, which is soon followed by plant necrosis.

In its free acid form, glyphosate has a low water solubility. As such, water-based glyphosate compositions typically contain a water soluble salt of glyphosate, such as the isopropylamine salt, ammonium salt, or trimesium salt.

The sulfosuccinate-based surfactants of the present invention may be prepared according to a two-step process. In the first step, a maleic ester is prepared by reacting an alkoxylated surfactant or a hydroxy-bearing hydrophobe with maleic anhydride or maleic acid. The term "hydroxy-bearing hydrophobe" includes, but is not limited to, linear and branched alcohols and their alkoxylates, alkylphenols and their alkoxylates, ethylene oxide/propylene oxide block copolymers, reverse block copolymers, and random copolymers. Hydroxy-bearing hydrophobe(s) may be a pure compound(s) or mixtures. The reaction may generally be conducted at a temperature of about 80° C., and in the presence of a catalyst. The water produced by the esterification reaction may be collected. When maleic anhydride (a similar reaction occurs with maleic acid) is used, the esterification reaction may be represented by the following equation, which is for illustrative purposes only, and is in no way meant to limit the scope of the present invention:

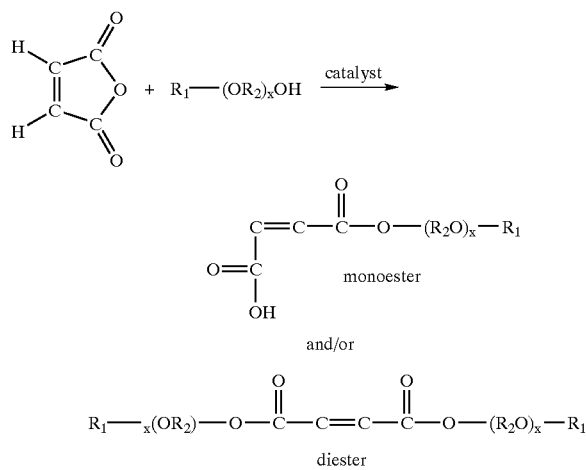

where $R_1$ is hydrogen or a straight or branched chain, unsaturated or saturated, alkyl, aryl, or alkylaryl group or mixtures thereof with from zero to about thirty carbon atoms; $R_2$ is an alkylene group with from about two to about six carbon atoms, or a mixture thereof; and x is the same or different, depending on whether ($R_2O$) is a pure compound or a mixture. In addition, x may vary from zero to about sixty. The products of the esterification reaction include monoesters and/or diesters.

In preparing the maleic ester, if an alkoxylated surfactant is used, the alkoxylated surfactant may include any number of suitable alkoxylated surfactants. Preferably, the alkoxylated surfactant includes, but is not limited to, linear alcohol alkoxylates (such as SURFONIC® L series surfactants), branched alcohol alkoxylates (such as SURFONIC® TDA, DDA, or DA series surfactants), alkylphenol alkoxylates (such as SURFONIC® N, OP, DDP, or DNP series surfactants), SURFONIC® POA series surfactants, or POGOL® series surfactants (all commercially available from the Huntsman Corporation, Houston, Tex.).

In preparing the maleic ester, if a hydroxy-bearing hydrophobe is used, the hydroxy-bearing hydrophobe may include any suitable hydroxy-bearing hydrophobe. In one embodiment of the present invention, the hydroxy-bearing hydrophobe includes, but is not limited to, linear and branched alcohol ethoxylates.

In preparing the maleic ester, the catalyst may comprise any catalyst that promotes the esterification reaction. In one embodiment of the present invention, the catalyst comprises p-toluenesulfonic acid.

In the second step, the maleic ester(s) prepared in step one are then sulfonated by reacting the ester(s) with a bisulfite salt to produce a sulfosuccinate product. The reaction may be conducted in a distillation vessel, at a temperature from about 60° C. to about 80° C. When an ammonium bisulfite salt (a similar reaction occurs with another bisulfite salt) is used, the reaction may be represented by the following equation, which is for illustrative purposes only, and is in no way meant to limit the scope of the claimed subject matter of the present invention:

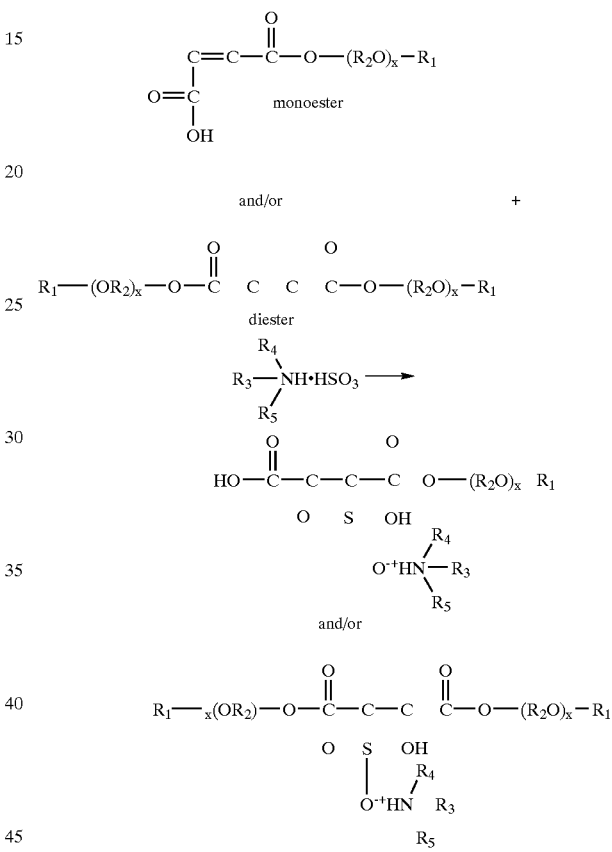

where $R_1$ is hydrogen or a straight or branched chain, unsaturated or saturated, alkyl, aryl, or alkylaryl group and mixtures thereof with from zero to about thirty carbon atoms; $R_2$ is an alkylene group with from about two to about six carbon atoms, or a mixture thereof; $R_3$, $R_4$, and $R_5$ are each independently hydrogen or a straight or branched chain, unsaturated or saturated, alkyl or alkyloxy group with from zero to about twenty-five carbon atoms and x is the same or different, depending on whether ($R_2O$) is a pure compound or a mixture. In addition, x may vary from zero to about sixty.

The sulfosuccinamate-based surfactants of the present invention may be prepared in a three-step process. In the first step, a carboxylic acid is reacted with a primary amine alkoxylate or a primary amine alcohol, to produce an amide product. The reaction may be conducted at a temperature from about 120° C. to about 140° C., and under nitrogen. The reaction should proceed until as much of the water from the reaction as practical has been collected. The amide preparation may be represented by the following equation:

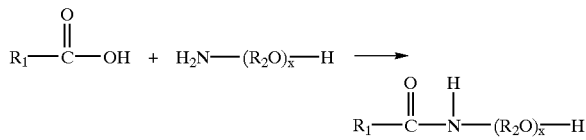

where $R_1$ is a straight or branched chain, unsaturated or saturated, alkyl, aryl, or alkylaryl group or mixtures thereof with from about one to about thirty carbon atoms; $R_2$ is either an alkylene group with from about two to about six carbon atoms, or a saturated or unsaturated alkyl, aryl, or alkylaryl group with from about one to about thirty carbon atoms; and x is the same or different, depending on whether $(R_2O)$ is a pure compound or a mixture. In addition, x may vary from zero to about sixty.

In the second step, the amide product may then be reacted with maleic anhydride or maleic acid to produce an ester. The esterification reaction may be conducted at a temperature of about 80° C., and in the presence of a catalyst. The water produced in the esterification reaction should be collected. When maleic anhydride (a similar reaction occurs with maleic acid) is used, the esterification reaction may be represented by the following equation, which is for illustrative purposes only, and is in no way meant to limit the scope of the claimed subject matter of the present invention:

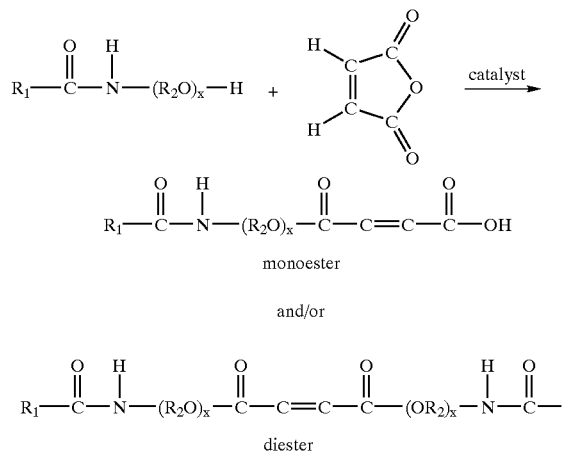

where $R_1$ is a straight or branched chain, unsaturated or saturated, alkyl, aryl, or alkylaryl group or mixtures thereof with from about one to about thirty carbon atoms; $R_2$ is either an alkylene group with from about two to about six carbon atoms, or a saturated or unsaturated alkyl, aryl, or alkylaryl group with from about one to about thirty carbon atoms; and x is the same or different, depending on whether $(R_2O)$ is a pure compound or a mixture. In addition, x may vary from zero to about sixty. The products of the esterification reaction include monoesters and/or diesters.

In the third step, the resulting maleic ester(s) may then be sulfonated by reacting the ester(s) with a bisulfite salt to produce a sulfosuccinamate product. The reaction may be conducted in a distillation flask, and at a temperature from about 60° C. to about 80° C. When an ammonium bisulfite salt is used, the reaction may be represented by the following equation, which is for illustrative purposes only, and is in no way meant to limit the scope of the claimed subject matter of the present invention:

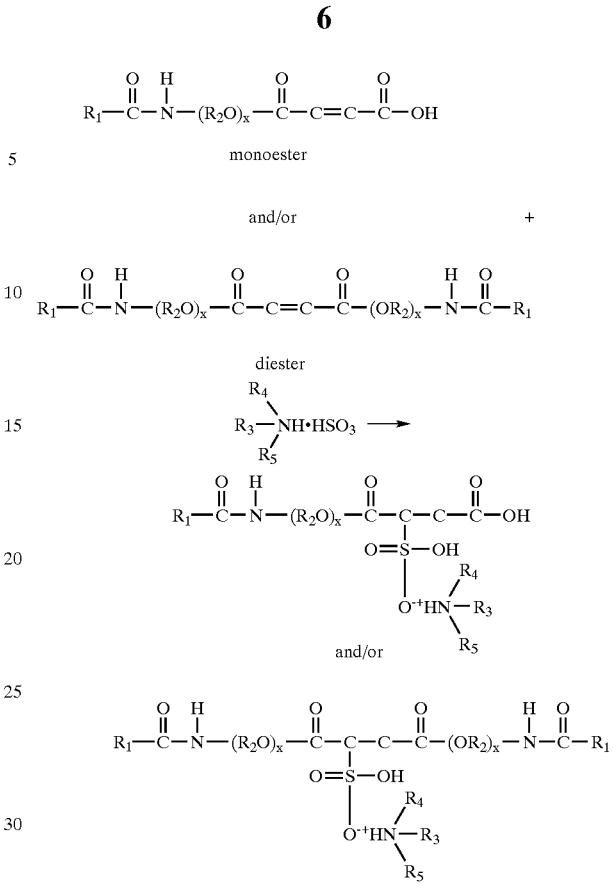

where $R_1$ is a straight or branched chain, unsaturated or saturated alkyl, aryl, or alkylaryl group or mixtures thereof with from about one to about thirty carbon atoms; $R_2$ is either an alkylene group with from about two to about six carbon atoms, or a saturated or unsaturated alkyl, aryl, or alkylaryl group with from about one to about thirty carbon atoms; $R_3$, $R_4$, and $R_5$ are each independently either a straight or branched chain, unsaturated or saturated alkyl or alkyloxy group with from zero to about twenty-five carbon atoms or hydrogen; and x is the same or different, depending on whether $(R_2O)$ is a pure compound or a mixture. In addition, x may vary from zero to about sixty.

In preparing the sulfosuccinate and the sulfosuccinamate-based surfactants, the bisulfite salt comprises isopropylammonium bisulfite. Isopropylammonium bisulfite may be prepared by reacting an isopropylamine-water solution with sulfur dioxide, in the presence of a 45% potassium hydroxide solution. During the progression of the reaction, the temperature and pressure of the reaction should be closely monitored. If the temperature exceeds about 40° C. during the addition of sulfur dioxide, the addition of sulfur dioxide should be halted until the temperature is reduced to about 30° C. Similarly, if the pressure exceeds about 20 psig, the addition of sulfur dioxide should be halted until the pressure is reduced to about 5 psig. The reaction is complete if the pressure stays above 20 psig for about 30 minutes, even after the addition of sulfur dioxide has been halted.

After preparation, the sulfosuccinate or sulfosuccinamate-based surfactant product may then be blended with a complementary amine-based surfactant. The amine-based surfactant comprises an alkoxylated amine. The amine-based surfactant may include, but is not limited to, polyoxyalkyleneamines (including, but not limited to, those that are commercially available under the JEFFAMINE® tradename from the Huntsman Corporation, Houston, Tex.), polyalkoxylate polyamines, cocoamine alkoxylates, soya amine alkoxylates, tallow amine alkoxylates, synthetic alkoxylated amines derived from primary alcohols, alkydiamine alkoxylates, etheramine alkoxylates, alkyletheramines, alkyletheramine alkoxylates, the methyl and ethyl quaternary ammonium salts thereof, and the amine oxides thereof (several of which are commercially available under the SURFONIC® T and OL trade names, from the Huntsman Corporation, Houston, Tex.).

After the sulfosuccinate or sulfosuccinamate-based surfactant is blended with an amine-based surfactant, the resulting surfactant mixture may then be blended with water or other formulation aids. Such formulation aids may include, but are not limited to, glycols (such as polyethylene glycols, polypropylene glycols, or glycol ethers), anti-freeze agents, dyes, thickening agents, anti-foaming agents, UV stabilizers, or pH adjusting agents that will cause the resulting surfactant mixture to have a neutral or slightly acidic pH (i.e. a pH of about 5.0 to about 7.5). The relative amount of water or other formulation aids that should be blended with the resulting surfactant mixture will depend on a variety of factors, including the pH of the resulting surfactant mixture, the nature of the herbicide to be blended with the surfactant solution, the proposed mode of application of the final herbicide formulation, the nature of the vegetation to be treated, etc.

If the surfactant compositions of the present invention are to be incorporated into glyphosate herbicides, preferably from about 25% to about 45% by mass of the surfactant composition should comprise a sulfosuccinate or sulfosuccinamate-based surfactant, from about 45% to about 60% by mass of the surfactant composition should comprise an amine-based surfactant, and from about 5% to about 20% by mass of the surfactant composition should comprise water or other formulation aids. "Surfactant composition" means the surfactants of the present invention blended with water and/or other formulation aids.

The surfactant compositions of the present invention may then be combined with a herbicide or a mixture of herbicides. Such herbicides may include, but are not limited to, the isopropylamine salt, ammonium salt, or trimesium salt of glyphosate, the ammonium salt of glufosinate, paraquat (1,1'Dimethyl-4,4'bipyridinium dichloride), or diquat (1,1'-ethylene-2,2'-bipyridylium dibromide). The relative amount of the surfactant compositions of the present invention that should be blended with a herbicide will vary depending on a variety of factors, including the nature of the herbicide, the nature of the vegetation to be treated, the method of application, whether the herbicide is to be formulated as a water-based or solid composition, etc. In any case, the resulting herbicide compositions of the present invention should include a herbicidally effective amount of a herbicidal active ingredient, and a sufficient amount of a surfactant of the present invention to enhance the effectiveness of the herbicidal active ingredient. The term "herbicidally effective amount", means the amount of herbicide necessary to promote plant necrosis.

The herbicide compositions of the present invention may be prepared as either liquid or solid compositions. Liquid compositions may include solutions ready for immediate application, aqueous concentrates intended to be diluted with water before application, or microencapsulated actives suspended in liquid media. Solid compositions may include, but are not limited to, water dispersible granules, water soluble granules, microencapsulated actives, free-flowing particulate compositions, or granular-based solids that have been compressed into tablets or briquets of any desired size and shape. Optionally, solid compositions may include formulations where the herbicide composition is absorbed onto water soluble or water insoluble inert dry carriers, including, but not limited to, Magnesol® (commercially available from the Dallas Group of America, Inc., Whitehouse, N.J.).

Accordingly, the herbicide compositions of the present invention may be applied to vegetation as either a liquid or solid composition. Liquid herbicide compositions are typically sprayed on the vegetation to be treated, and typically comprise either liquid concentrates or dissolved or dispersed solid compositions. Liquid compositions may also be injected into, or painted on the trunk portion of the vegetation to be treated. Solid granular compositions may be spread on or around the vegetation to be treated.

Herbicide formulations comprising the surfactant compositions of the present invention have a reduced tendency to cause eye and skin irritation. Reduced eye and skin irritation is expected because the pH of the surfactant compositions of the present invention is about 7.0. Because herbicides are often applied by humans, or in the vicinity of humans or animals, reduced eye irritation is a desirable feature in such compositions.

It is understood that variations may be made in the foregoing without departing from the scope of the invention. For example, although the surfactants of the present invention are primarily discussed as being incorporated into water-based herbicide compositions, it is understood that the surfactants of the present invention may also be incorporated into dry granular herbicide formulations. In addition, although the surfactants of the present invention are primarily discussed as being incorporated into glyphosate solutions, the surfactants of the present invention may be incorporated into any number of other herbicide formulations, including, but not limited to, macro and micro emulsions, suspension, suspension concentrates, and other liquid and solid formulations known to those skilled in the art, to increase the bioefficacy of such herbicides.

The following examples are illustrative of the present invention, and are not intended to limit the scope of the invention in any way.

Preparation of a Sulfosuccinate Surfactant

Preparation of the Maleic Ester

EXAMPLE 1a 928.8 grams of SURFONIC® L24-4, 271.2 grams of maleic anhydride, and 12.0 grams of p-toluenesulfonic acid were charged to a three neck flask, and heated to a temperature of about 80° C. The mixture was then heated at this temperature for about four hours, and the water produced in the esterification reaction was collected. The mixture was then allowed to cool.

Preparation of Isopropylammonium Bisulfite

EXAMPLE 1b

A two-stage caustic trap was assembled, with 500 grams of a 45% potassium hydroxide solution in each flask of the vent. 768 grams of an isopropylamine-water solution were then charged to a padded reaction vessel, the agitator was turned on, and cool water was circulated through the padded reaction vessel. 227 grams of sulfur dioxide were then charged through the oxide feed line. Sulfur dioxide was then added at a rate of 0.05 lbs/minute, as the temperature and pressure of the reaction was closely monitored. If the temperature exceeded about 40° C., the addition of sulfur dioxide was halted until the temperature was reduced to about 30° C. If the pressure exceeded about 20 psig, the addition of sulfur dioxide was also halted until the pressure was reduced to about 5 psig. The reaction was completed once the pressure remained at about 20 psig for about 30 minutes, even after sulfur dioxide addition had been halted. After completion of the reaction, the reaction vessel was purged with nitrogen for about 30 minutes through the trap system.

Preparation of the Sulfonated Maleic Ester

EXAMPLE 1c 149.4 grams of the SURFONIC® L24-4 maleic ester produced in Example 1a were charged to a three neck distillation flask, and heated to a temperature of about 60° C. Then, 101.3 grams of the isopropylammonium bisulfite produced in Example 1b were added drip-wise to the distillation flask. After all the isopropylammonium bisulfite had been added to the distillation flask, the reaction components were heated at a temperature of about 80° C. for about 2 hours. The resulting product was then allowed to cool.

$^{13}$C NMR confirmed that the resulting product was a sulfosuccinate-based product.

Preparation of the Blended Sulfosuccinate Surfactant Adjuvant

EXAMPLE 2

The sulfosuccinate-based surfactant prepared in Example 1c was then blended with an amine-based surfactant and water, in the following proportions:

| Adjuvant | Sulfosuccinate-Based Surfactant from Example 1c | Water | Amine-Based Surfactant |
|---|---|---|---|
| A | 25.6% | 14.9% | 5.9% (SURFONIC® T-2)[1] 53.6% (SURFONIC® T-15)[2] |
| B | 44.0% | 11.0% | 45.0% (SURFONIC® T-10)[3] |
| C | 27.2% | 14.7% | 58.1% (ethylene diamine + 4PO + 20EO) |
| D | 73.0% | 5.0% | 22.0% (ethylene diamine + 4PO) |

[1,2,3]Commercially available from the Huntsman Corporation, Houston, Texas.

Bioefficacy Testing of Glyphosate Solutions Containing a Sulfosuccinate Surfactant Adjuvant of the Present Invention

EXAMPLE 3

Each of the adjuvant solutions prepared in Example 2 was then blended with a glyphosate solution, so that the final solutions contained 7.5%, 15%, and 30% of the adjuvant solution prepared in Example 2. Rodeo® was used as the source of glyphosate. (Rodeo® contains 648 g/L of the mono-isopropylamine salt of glyphosate.)

An outside laboratory conducted bioefficacy testing using the blended glyphosate solutions. Bioefficacy testing was conducted on pitted morning glory, lambs quarters, and velvet leaf weeds. For comparison, the laboratory also tested the bioefficacy of a glyphosate solution that did not contain a surfactant, namely, Rodeo®, and a glyphosate solution that contained an ethoxylated etheramine, namely Roundup®Ultra (commercially available from the Monsanto Company, St. Louis, Mo.).

Each of the subject weeds was sprayed with the various glyphosate solutions, and the observed plant necrosis was noted seven and fourteen days after treatment. The results of the bioefficacy testing, seven days after treatment, are summarized in Table 1. The results are expressed in terms of percent plant necrosis, where 0% represents no plant necrosis, and 100% represents complete plant necrosis.

TABLE 1

| Glyphosate Solution | Morning Glory (% plant necrosis) | Lambs Quarters (% plant necrosis) | Velvet Leaf (% plant necrosis) |
|---|---|---|---|
| Rodeo® | 43 | 0 | 31 |
| Roundup® Ultra | 48 | 46 | 56 |
| A (7.5%) | 45 | 38 | 40 |
| A (15%) | 43 | 45 | 49 |
| A (30%) | 46 | 45 | 39 |
| B (7.5%) | 46 | 44 | 36 |
| B (15%) | 46 | 40 | 41 |
| B (30%) | 45 | 45 | 40 |
| C (7.5%) | — | 16 | 40 |
| C (15%) | — | 19 | 46 |
| C (30%) | — | 21 | 53 |
| D (7.5%) | — | 11 | 46 |
| D (15%) | — | 13 | 36 |
| D (30%) | — | 10 | 33 |

The results of the bioefficacy testing, fourteen days after treatment, are summarized in Table 2. The results are expressed in terms of percent plant necrosis, where 0% represents no plant necrosis, and 100% represents complete plant necrosis.

TABLE 2

| Glyphosate Solution | Morning Glory (% plant necrosis) | Lambs Quarters (% plant necrosis) | Velvet Leaf (% plant necrosis) |
|---|---|---|---|
| Rodeo® | 71 | 0 | 38 |
| Roundup® Ultra | 71 | 78 | 70 |
| A (7.5%) | 69 | 68 | 60 |
| A (15%) | 71 | 73 | 65 |
| A (30%) | 75 | 83 | 85 |
| B (7.5%) | 71 | 70 | 63 |
| B (15%) | 74 | 65 | 78 |
| B (30%) | 69 | 78 | 78 |
| C (7.5%) | — | 10 | 73 |
| C (15%) | — | 13 | 76 |
| C (30%) | — | 28 | 80 |
| D (7.5%) | — | 18 | 60 |
| D (15%) | — | 28 | 65 |
| D (30%) | — | 30 | 60 |

Referring to Tables 1 and 2, it is apparent that the addition of the adjuvants of the present invention to glyphosate herbicide compositions generally improved the herbicidal efficacy of such glyphosate formulations, as compared to formulations with no adjuvant. In addition, several of the glyphosate solutions containing the adjuvants of the present invention also surpassed the bioefficacy of the Roundup®Ultra solution.

Preparation of a Sulfosuccinamate Surfactant

Preparation of the Amide

EXAMPLE 4a 316.9 grams of isopropanol amine and 1183.1 grams of oleic acid were charged to a two liter, three neck boiling flask, and chilled water was circulated through the condenser. The reaction products were then stirred, and heated to a temperature from about 120° C. to about 140° C., under nitrogen. Heating was continued until no more water was collected. The reaction mixture was then allowed to cool.

Preparation of the Maleic Ester

EXAMPLE 4b 907.0 grams of the isopropanol oleamide prepared in Example 4a, 293.0 grams of maleic anhydride, and 12.0 grams of p-toluenesulfonic acid were charged to a three neck distillation pot. The reaction components were then heated to a temperature of about 80° C., under nitrogen, for about seven hours, and the water produced in the esterification reaction was collected.

Preparation of the Sulfonated Maleic Ester

EXAMPLE 4c 149.4 grams of the maleic ester produced in Example 4b were charged to a three neck distillation flask, and heated to a temperature of about 60° C. Then, 101.3 grams of the isopropylammonium bisulfite produced in Example 1b were added drip-wise to the distillation flask. After all the isopropylammonium bisulfite had been added to the distillation flask, the reaction components were heated at a temperature of about 80° C. for about 2 hours. The resulting product was then allowed to cool.

Preparation of the Blended Sulfosuccinamate Surfactant Adjuvant

EXAMPLE 5

The sulfosuccinamate-based surfactant prepared in Example 4c was then blended with an amine-based surfactant, namely, a tallow amine ethoxylate (commercially available from the Huntsman Corporation, Houston, Tex.), and water. The components were blended in the following amounts:

| Component | Amount (%) |
| --- | --- |
| Sulfonated Maleic Ester prepared in Example 4c | 25.6 |
| Tallow amine ethoxylate | 59.5 |
| Water | 14.9 |

Bioefficacy Testing of Glyphosate Solutions Containing a Sulfosuccinamate Surfactant Adjuvant of the Present Invention EXAMPLE 6 (Prophetic)

The surfactant solution prepared in Example 5 is blended with a glyphosate solution. Rodeo® can be used as the source of glyphosate. (Rodeo® contains 648 g/L of the mono-isopropylamine salt of glyphosate.)

The glyphosate solution containing the surfactant adjuvant of the present invention is then sprayed on a variety of weeds. The weeds are examined approximately fourteen days after treatment with the glyphosate solution. The weeds appear to be significantly affected by the treatment, and most appear to be dead.

Although illustrative embodiments have been shown and described, a wide range of modification, changes, and substitution is contemplated in the foregoing disclosure. In some instances, some features of the disclosed embodiments may be employed without a corresponding use of the other features. Accordingly, it is appropriate that the appended claims be construed broadly and in a manner consistent with the scope of the invention.

What is claimed is:

1. A herbicide composition that comprises:

a. a herbicidally effective amount of a herbicidal active ingredient; and b. a surfactant component comprising an amine-based surfactant and a sulfosuccinate or sulfosuccinamate-based surfactant, wherein the surfactant component is present in an amount sufficient to enhance the effectiveness of the herbicidal active ingredient, and wherein the sulfosuccinate-based surfactant comprises a sulfosuccinate with the following general structure:

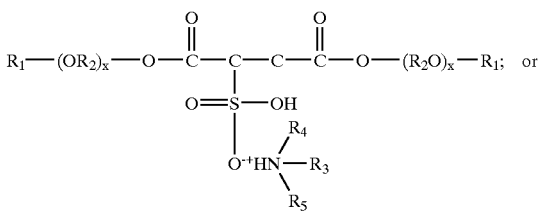

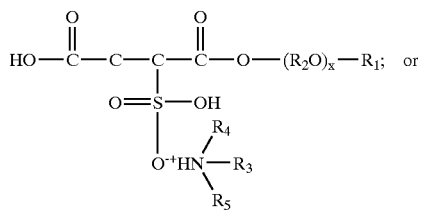

a mixture of (a) and (b);

where $R_1$ is hydrogen, or a straight or branched chain, unsaturated or saturated alkyl, aryl, or alkylaryl group with from zero to about thirty carbon atoms; $R_2$ is an alkylene group with from about two to about six carbon atoms, or a mixture thereof; $R_3$, $R_4$, and $R_5$ are each independently hydrogen, or a straight or branched chain, unsaturated or saturated alkyl or alkyloxy group with from zero to about twenty-five carbon atoms; and, x is the same or different and may vary from zero to about sixty, and wherein the sulfosuccinamate-based surfactant comprises a sulfosuccinamate with following general structure:

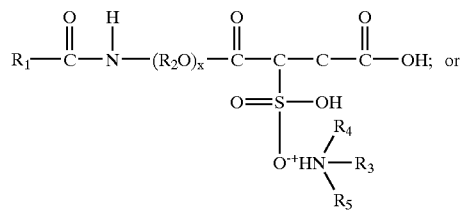

-continued

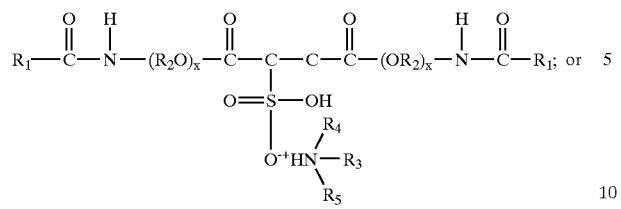

(b)

a mixture of (a) and (b);
where $R_1$ is a straight or branched chain, unsaturated or saturated alkyl, aryl, or alkylaryl group or mixtures thereof with from about one to about thirty carbon atoms; $R_2$ is either an alkylene group with from about two to about six carbon atoms, or a saturated or unsaturated alkyl, aryl, or alkylaryl group with from about one to about thirty carbon atoms; $R_3$, $R_4$, and $R_5$ are each independently hydrogen, or a straight or branched chain, unsaturated or saturated alkyl or alkyloxy group with from zero to about twenty-five carbon atoms; and, x is the is the same or different and may vary from zero to about sixty.

2. The composition of claim 1, wherein the amine-based surfactant comprises an alkoxylated amine surfactant.

3. The composition of claim 2, wherein the alkoxylated amine surfactant is selected from the group consisting of polyoxyalkyleneamines, polyalkoxylate polyamines, cocoamine alkoxylates, tallow amine alkoxylates, soya amine alkoxylates, synthetic alkoxylated amines derived from primary alcohols, alkydiamine alkoxylates, etheramine alkoxylates, alkyletheramines, alkyletheramine alkoxylates, the methyl and ethyl quaternary ammonium salts thereof, and the amine oxides thereof.

4. The composition of claim 1, wherein the herbicidal active ingredient comprises glyphosate or a salt thereof.

5. The composition of claim 1, wherein the surfactant component further comprises water and a formulation aid.

6. The composition of claim 5, wherein the formulation aid is selected from the group consisting of glycols, antifreeze agents, dyes, thickening agents, anti-foaming agents, UV stabilizers, pH adjusting agents, and mixtures thereof.

7. The composition of claim 6, wherein the composition has a reduced tendency to cause eye and skin irritation.

8. A herbicide composition that comprises:
a. a herbicidally effective amount of glyphosate or a salt thereof; and
b. a surfactant component comprising an amine-based surfactant, and a sulfosuccinate or sulfosuccinamate-based surfactant, wherein the surfactant component is present in an amount sufficient to enhance the effectiveness of the herbicidal active ingredient, and wherein the sulfosuccinate-based surfactant comprises a sulfosuccinate with following general structure:

(a)

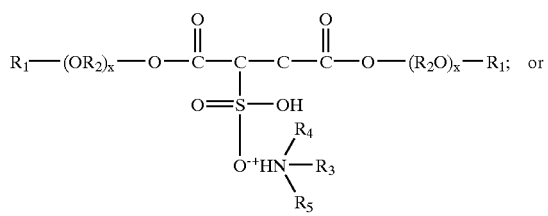

or

-continued

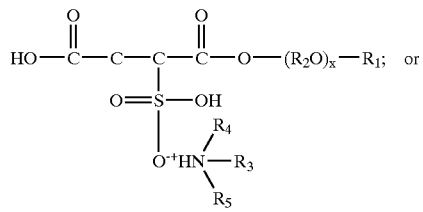

(b)

a mixture of (a) and (b);
where $R_1$ is hydrogen, or a straight or branched chain, unsaturated or saturated alkyl, aryl, or alkylaryl group or mixtures thereof with from zero to about thirty carbon atoms; $R_2$ is an alkylene group with from about two to about six carbon atoms, or a mixture thereof; $R_3$, $R_4$, and $R_5$ are independently hydrogen, or a straight or branched chain, unsaturated or saturated alkyl or alkyloxy group with from zero to about twenty-five carbon atoms; and, x is the same of different and may vary from 0 to 60, and wherein the sulfosuccinamate-based surfactant comprises a sulfosuccinamate with following general structure:

(a)

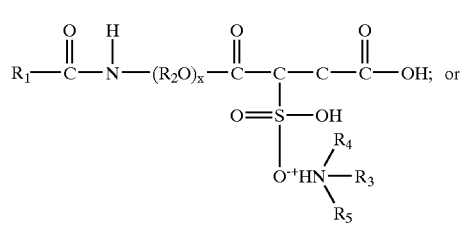

(b)

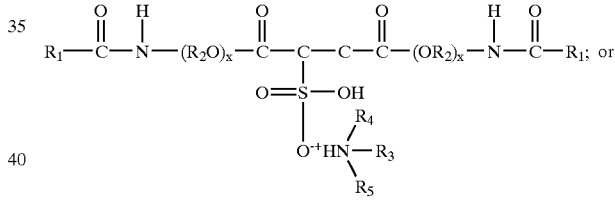

a mixture of (a) and (b);
where $R_1$ is a straight or branched chain, unsaturated or saturated alkyl, aryl, or alkylaryl group or mixtures thereof with from about one to about thirty carbon atoms; $R_2$ is either an alkylene group with from about two to about six carbon atoms, or a saturated or unsaturated alkyl, aryl, or alkylaryl group with from about one to about thirty carbon atoms; $R_3$, $R_4$, and $R_5$ are each independently hydrogen, or a straight or branched chain, unsaturated or saturated alkyl or alkyloxy group with from zero to about twenty-five carbon atoms; and, x is the same or different and may vary from zero to about sixty.

9. The composition of claim 8, wherein the amine-based surfactant comprises an alkoxylated amine surfactant.

10. The composition of claim 9, wherein the alkoxylated amine surfactant is selected from the group consisting of polyoxyalkyleneamines, polyalkoxylate polyamines, cocoamine alkoxylates, tallow amine alkoxylates, soya amine alkoxylates, synthetic alkoxylated amines derived from primary alcohols, alkydiamine alkoxylates, etheramine alkoxylates, alkyletheramines, alkyletheramine alkoxylates, the methyl and ethyl quaternary ammonium salts thereof, and the amine oxides thereof.

11. The composition of claim 8, wherein the surfactant component further comprises water and a formulation aid.

12. The composition of claim 11, wherein the formulation aid is selected from the group consisting of anti-freeze agents, dyes, thickening agents, anti-foaming agents, pH adjusting agents, and mixtures thereof.

13. The composition of claim 8, wherein from about 25% to about 45% by mass of the surfactant component comprises the sulfosuccinate or sulfosuccinamate-based surfactant.

14. The composition of claim 8, wherein from about 45% to about 60% by mass of the surfactant component comprises the amine-based surfactant.

15. The composition of claim 8, wherein from about 5% to about 20% by mass of the surfactant component comprises water and a formulation aid.

16. The composition of claim 8, wherein the composition has a reduced tendency to cause eye and skin irritation.

17. A method of killing or controlling weeds or unwanted vegetation comprising the step of applying a herbicidally effective amount of the composition of claim 1 to the foliage or tissue of the weeds or unwanted vegetation.

18. A method of killing or controlling weeds or unwanted vegetation comprising the step of applying a herbicidally effective amount of the composition of claim 8 to the foliage or tissue of the weeds or unwanted vegetation.

19. A method of preparing a herbicidally effective composition comprising the steps of:

a. blending a surfactant component comprising an amine-based surfactant and a sulfosuccinate or sulfosuccinamate-based surfactant, wherein the sulfosuccinate-based surfactant comprises a sulfosuccinate with following general structure:

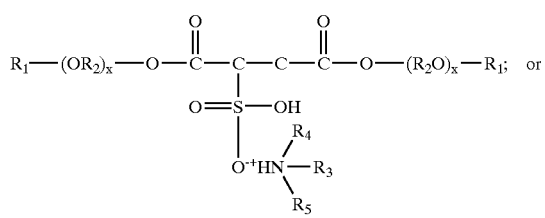

(a)

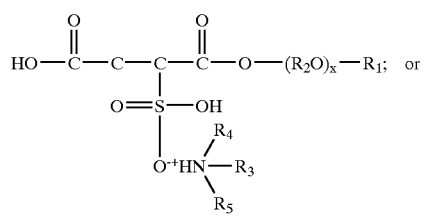

(b)

a mixture of (a) and (b);

where $R_1$ is hydrogen, or a straight or branched chain, unsaturated or saturated alkyl, aryl, or alkylaryl group or mixtures thereof with from zero to about thirty carbon atoms; $R_2$ is an alkylene group with from about two to about six carbon atoms, or a mixture thereof; $R_3$, $R_4$, and $R_5$ are each independently hydrogen, or a straight or branched chain, unsaturated or saturated alkyl or alkyloxy group with from zero to about twenty-five carbon atoms; and, x is the same or different and may vary from zero to about sixty, and wherein the sulfosuccinamate-based surfactant comprises a sulfosuccinamate with following general structure:

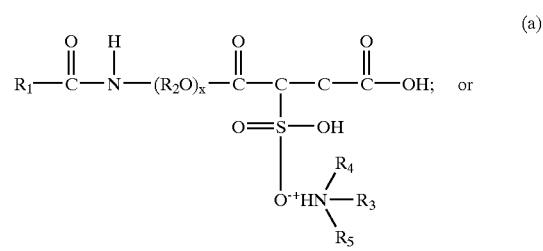

(a)

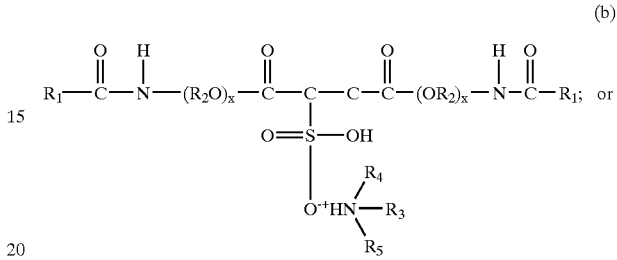

(b)

a mixture of (a) and (b);

where $R_1$ is a straight or branched chain, unsaturated or saturated alkyl, aryl, or alkylaryl group or mixtures thereof with from about one to about thirty carbon atoms; $R_2$ is either an alkylene group with from about two to about six carbon atoms, or a saturated or unsaturated alkyl, aryl, or alkylaryl group with from about one to about thirty carbon atoms; $R_3$, $R_4$, and $R_5$ are each independently hydrogen, or a straight or branched chain, unsaturated or saturated alkyl or alkyloxy group with from zero to about twenty-five carbon atoms; and, x is the same or different and may vary from zero to about sixty; and b. mixing a sufficient amount of the surfactant component with a herbicidal active ingredient to enhance the effectiveness of the herbicidal active ingredient.

20. The method of claim 19, wherein the amine-based surfactant comprises an alkoxylated amine surfactant.

21. The method of claim 19, wherein the alkoxylated amine surfactant is selected from the group consisting of polyoxyalkyleneamines, polyalkoxylate polyamines, cocoamine alkoxylates, tallow amine alkoxylates, soya amine alkoxylates, synthetic alkoxylated amines derived from primary alcohols, alkydiamine alkoxylates, etheramine alkoxylates, alkyletheramines, alkyletheramine alkoxylates, the methyl and ethyl quaternary ammonium salts thereof, and the amine oxides thereof.

22. The method of claim 19, wherein the herbicidal active ingredient comprises glyphosate or a salt thereof.

23. The method of claim 19, wherein the surfactant component further comprises water and a formulation aid.

24. The method of claim 23, wherein the formulation aid is selected from the group consisting of glycols, anti-freeze agents, dyes, thickening agents, anti-foaming agents, UV stabilizers, pH adjusting agents, and mixtures thereof.

25. A method of preparing a composition, comprising the steps of:

a. blending a surfactant component comprising an amine-based surfactant and a sulfosuccinate or sulfosuccinamate-based surfactant, and b. mixing a sufficient amount of the surfactant component with a herbicidal active ingredient to enhance the effectiveness of the herbicidal active ingredient, wherein a herbicidally effective composition having a reduced tendency to cause eye and skin irritation is produced.

* * * * *